United States Patent
Albers et al.

(10) Patent No.: US 6,605,069 B1
(45) Date of Patent: Aug. 12, 2003

(54) AROMATIC COPOLYESTER CONTAINING ACTIVE INGREDIENTS

(75) Inventors: Reinhard Albers, Leverkusen (DE); Ralf Dujardin, Willich (DE); Heinz Pudleiner, Krefeld (DE); Joachim Simon, Düsseldorf (DE); Rita Fröde, Monheim (DE); Hartwin Hobler, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/831,232

(22) PCT Filed: Nov. 2, 1999

(86) PCT No.: PCT/EP99/08354

§ 371 (c)(1),
(2), (4) Date: May 7, 2001

(87) PCT Pub. No.: WO00/28815

PCT Pub. Date: May 25, 2000

(30) Foreign Application Priority Data

Nov. 12, 1998 (DE) .......................................... 198 52 192

(51) Int. Cl.⁷ .......................... A61M 5/00; A61M 25/00; A61K 9/00; A61K 9/14; A01N 25/00
(52) U.S. Cl. ........................ 604/264; 604/265; 424/400; 424/405; 424/486; 424/489; 424/497
(58) Field of Search ................................. 424/405, 486, 424/400, 489, 497; 604/264, 265

(56) References Cited

U.S. PATENT DOCUMENTS

| | | | |
|---|---|---|---|
| 3,023,192 A | * 2/1962 | Shivers | |
| 5,019,096 A | 5/1991 | Fox, Jr. et al. | 623/1 |
| 5,165,952 A | 11/1992 | Solomon et al. | 427/2 |
| 5,556,383 A | 9/1996 | Wang et al. | 604/96 |
| 5,616,338 A | 4/1997 | Fox, Jr. et al. | 424/423 |
| 5,840,323 A | * 11/1998 | Taha et al. | |

FOREIGN PATENT DOCUMENTS

| | | |
|---|---|---|
| DE | 2239271 | 2/1973 |
| WO | 96/22114 | * 7/1996 |

OTHER PUBLICATIONS

Patent Abstract of Japan, vol. 1997, No. 02, Feb. 28, 1997, & JP 08 280790 A (Otsuka Pharmaceut Factory Inc.) Oct. 29, 1996, Zusammenfassung & Database WPI Week 9702, Derwent Publication Ltd., London, GB; An 1997–015196, XP002135906 & JP 08 280790A.

Schierholz J.M. et al: "Controlled release of antibiotics from biomedical polyurethanes: Morphological and structural features", Biomaterials, GB, Elsevier Science Publishers BV., Barking, Bd. 18, Nr. 12, Jan. 1, 1997, Seiten 839–844, XP004064466.

* cited by examiner

Primary Examiner—Thurman K. Page
Assistant Examiner—Humera N. Sheikh
(74) Attorney, Agent, or Firm—Joseph C. Gil; Aron Preis; James R. Franks

(57) ABSTRACT

The invention relates to aromatic copolyesters comprising antimicrobially active substances in homogeneous distribution, processes for their preparation and their use in medical articles.

12 Claims, No Drawings

AROMATIC COPOLYESTER CONTAINING ACTIVE INGREDIENTS

The invention relates to aromatic copolyesters comprising antimicrobially active substances in homogeneous distribution, processes for their preparation and their use in medical articles.

Vascular, catheter-associated infections are an important cause of morbidity and mortality in patients in intensive care. Recent studies demonstrate that in this group of patients up to 16% of those carrying catheters suffer from a catheter-induced sepsis. Approx. 2% of these patients show serious clinical complications, in particular septic shock or acute organ failure. An incidence of catheter infections which will increase further is to be expected in the future, since catheters are increasingly being used in modern intensive care treatment for invasive monitoring or treatment strategies, such as e.g. continuous haemofiltration.

Numerous studies have shown that coagulase-negative Staphylococci, the transient microbe Staphylococcus aureus and various Candida species are the main causative organisms of catheter-associated infections. These microorganisms, which are ubiquitous on the skin, penetrate through the physiological skin barrier when the catheter is applied and in this way enter into the subcutaneous region and fin ally into the bloodstream. Adhesion of the bacteria to the surface of the plastic is regarded as an essential step in the pathogenesis of foreign body infections. After adhesion of the skin microbes on to the polymer surface, proliferation of the bacteria follows, with colonization of the polymer. This is accompanied by a production of a biofilm by bacterial excretion of extracellular glycocalix. The biofilm assists adhesion of the pathogens and protects them from the body's own immune defence. The biofilm furthermore forms a barrier which is impenetrable to many antibiotics. After increased proliferation of the pathogenic microbes on the polymer surface, septic bacteriaemia may finally occur. Removal of the infected catheter is necessary for treatment of such infections, since chemotherapy with antibiotics would require non-physiologically high doses.

The use of central venous catheters therefore not only involves a high risk of infection for the patient, but also causes enormous secondary treatment costs.

These problems can be only partly solved by prophylactic measures, such as e.g. hygiene measures or routine endoluminal administration of antibiotics. A rational strategy for prevention of polymer-associated infections consists of modification of the polymeric materials used. The aim of this modification must be inhibition of the adhesion of bacteria and of proliferation of already-adhered bacteria, so that foreign body infections can be avoided causally in this way. This can be achieved e.g. by incorporating a suitable antimicrobially active substance into the polymer matrix (e.g. antibiotics), provided that the active compound incorporated can also diffuse out of the polymer matrix. In this case the release of the active compound can be extended over a relatively long period of time, so that the adhesion of bacteria and proliferation on the polymer is prevented for an appropriately longer period of time.

Methods for the preparation of antimicrobially equipped polymers for medical uses are already known. In the numerous processes described, the active compound is added by the following techniques:

a) Adsorption on to the polymer surface (passively or via surfactants)
b) Introduction into a polymer coating which is applied to the surface of a shaped article
c) Incorporation into the bulk phase of the polymeric carrier material
d) Covalent bonding to the polymer surface DE-A-41 43 239 discloses, for example, a process for introducing active compounds into the outer layer of medical articles (impregnation). In this process, the implantable device of polymeric material is swollen in a suitable solvent. The polymer matrix is changed here such that a pharmaceutical active compound or an active compound combination can penetrate into the polymeric material of the implant. After removal of the solvent the active compound is enclosed in the polymer matrix. After contact with physiological medium the active compound contained in the implantable device is released again by diffusion. The release profile here can be adjusted by the choice of solvent and by varying the experimental conditions.

Polymer materials for medical uses which have coatings comprising active compounds are mentioned, for example, in EP-A 328 421. Processes for the preparation of the antimicrobially active coatings and methods for application to the surfaces of medical devices are described. The coatings comprise a polymer matrix, in particular of polyurethanes, silicones or biodegradable polymers, and an antimicrobially active substance, preferably a synergistic combination of a silver salt with chlorhexidine or an antibiotic.

All the processes mentioned have the common feature that equipping the medical working means with a pharmacologically active substance necessitates an additional working step, that is to say either pretreatment of the polymer material before processing or after-treatment of the shaped articles produced. This causes additional costs and involves an increased consumption of time on production. Another problem of the processes lies in the use of organic solvents, which usually cannot be removed without trace from the material.

The object of the invention was to provide new polymer materials which are suitable for the production of medical shaped articles for short-term implants, in particular catheters, and efficiently prevent colonization of the surface by microbes for a relatively long period of time (2–4 weeks).

Aromatic copolyesters which comprise antimicrobially active substances in homogeneous distribution and which release at the surface over a relatively long period of time a concentration of an antimicrobially active substance which suppresses colonization with germs have now been found. The invention therefore provides aromatic copolyesters which comprise an antimicrobially active substance in homogeneous distribution.

Possible antimicrobially active substances are in principle all active compounds which have a broad action spectrum against the pathogenic microorganisms involved in polymer-associated infections, in particular against coagulase-negative Staphylococci, Staphylococcus aureus and Candida species. The antimicrobially active substances can also be used according to the invention as active compound combinations in the shaped articles, as long as they are not antagonistic in their actions.

The active compound used must have an adequate (chemical) stability in the polymer matrix. Furthermore, the microbiological activity of the active compound must not be impaired in the polymer matrix and under the process conditions of incorporation, and the active compound must thus be stable at the temperatures of 150 to 200° C. required for thermoplastic processing of the polymeric material.

The incorporation of the pharmaceutically active substance should impair neither the biocompatibility of the polymer surface nor other desirable polymer-specific properties of the polymeric material (elasticity, tear strength etc.).

Suitable substances having an antibiotic action are, for example:

- earlier quinolones, such as e.g. nalidixic acid, pipemidic acid and cinoxacin,
- more recent quinolones, such as e.g. ciprofloxacin, norfloxacin, ofloxacin, pefloxacin and enoxacin, preferably ciprofloxacin,
- aminoglycosides, such as e.g. gentamycin, kanamycin, amikacin, sisomycin, tobramycin and netilmicin, preferably gentamycin and kanamycin,
- macrolides, such as e.g. erythromycin, clarithromycin and azithromycin,
- polypeptides, such as e.g. bacitracin, mupirocin and thyrothricin (combination of gramicidin and tyrocidin,
- lincomycins, such as e.g. lincomycin and clindamycin
- antimycobacterial agents, such as e.g. rifampicin or fusidic acid.

The antimicrobially active substance can also be an antiseptic or a disinfectant, as long as the substance used has an adequate activity against the infection-causing species.

Substances (pro-drugs) which release an antimicrobially active substance after the influence of microbial activity can moreover be employed.

The active compounds are preferably incorporated in a concentration corresponding to their antimicrobial activity. The active compounds are particularly preferably used in a concentration range of 0.01 to 10.0 wt. %.

Suitable copolyesters (segmented polyester elastomers) are built up, for example, from a large number of recurring, short-chain ester units and long-chain ester units which are combined by ester bonds, wherein the short-chain ester units make up about 15–65 wt. % of the copolyester and have the formula (I)

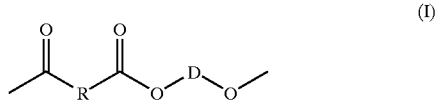

(I)

in which
R represents a divalent radical of a dicarboxylic acid which has a molecular weight of less than about 350,
D represents a divalent radical of an organic diol which has a molecular weight of less than about 250;
the long-chain ester units make up about 35–85 wt. % of the copolyester and have the formula II

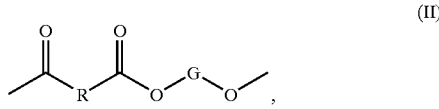

(II)

in which
R represents a divalent radical of a dicarboxylic acid which has a molecular weight of less than about 350,
G represents a divalent radical of a long-chain glycol which has an average molecular weight of about 350 to 6,000.

The copolyesters which can be used according to the invention can be prepared by a procedure in which a) one or more dicarboxylic acids, b) one or more linear, long-chain glycols and c) one or more low molecular weight diols are polymerized with one another.

The dicarboxylic acids for the preparation of the copolyester are the aromatic acids having 8–16 C atoms, in particular phenylenedicarboxylic acids, such as phthalic, terephthalic and isophthalic acid.

The low molecular weight diols for the reaction to form the short-chain ester units of the copolyesters belong to the classes of acyclic, alicyclic and aromatic dihydroxy compounds. The preferred diols have 2–15 C atoms, such as ethylene, propylene, tetramethylene, isobutylene, pentamethylene, 2,2-dimethyltrimethylene, hexamethylene and decanethylene glycols, dihydroxycyclohexane, cyclohexanedimethanol, resorcinol, hydroquinone and the like. The bisphenols for the present purpose include bis-(p-hydroxy)-diphenyl, bis-(p-hydroxyphenyl)-methane, bis-(p-hydroxyphenyl)-ethane and bis-(p-hydroxyphenyl)-propane.

The long-chain glycols for the preparation of the soft segments of the copolyesters preferably have molecular weights of about 600 to 3,000. These include poly-(alkylene ether)-glycols, in which the alkylene groups have 2–9 carbon atoms.

Glycol esters of poly-(alkylene oxide)-dicarboxylic acids or polyester glycols can also be used as the long-chain glycol.

The long-chain glycols also include polyformals, which are obtained by reaction of formaldehyde with glycols. Polythioether glycols are also suitable. Polybutadiene glycols and polyisoprene glycols, copolymers thereof and saturated hydrogenation products of these materials are satisfactory long-chain polymeric glycols.

Processes for the synthesis of such copolyesters are known from DE-OS 2 239 271, DE-OS 2 213 128, DE-OS 2 449 343 and U.S. Pat. No. 3 023 192.

The copolyesters described are characterized by a very good profile of mechanical properties. The Shore hardness can be varied over a wide range (Short 70 A-Shore 60 D), depending on the composition of the copolyesters. Compared with thermoplastic polyurethanes (TPU), the moduli of the copolyesters at the same hardness are at a significantly higher level.

On the basis of these specific properties, the copolyesters are suitable for the production of medical devices, in particular for uses in transluminal angioplasty (balloon dilation).

The copolyesters according to the invention comprising active compounds can furthermore comprise the conventional additives for plastics. Conventional additives are, for example, lubricants, such as fatty acid esters, metal soaps thereof, fatty acid amides and silicone compounds, antiblocking agents, inhibitors, stabilizers against hydrolysis, light, heat and discoloration, flameproofing agents, dyestuffs, pigments, inorganic or organic fillers and reinforcing agents. Reinforcing agents are, in particular, fibrous reinforcing substances, such as inorganic fibres, which are prepared according to the prior art and can also be charged with a size. Further details of the auxiliary substances and additives mentioned can be found in the technical literature, for example R. Gachter, H. Muller (ed.): Taschenbuch der Kunststoff-Additive [Pocket Book of Plastics Additives], 3rd edition, Hanser Verlag, Munich 1989, or DE-A 29 01 774.

Systematic studies have shown that a homogeneous distribution of the antimicrobially active substance in the polymer matrix is necessary in order to be able to utilise the diffusion of the active compound as an adjustable release mechanism. The antimicrobially active substance and the polymeric carrier material used should therefore have a high physico-chemical compatibility. The interfacial energy which arises in the system is a measure of the compatibility of the active compound and matrix. If this is high, the active compound and matrix are not very compatible and the active compound is released rapidly. If the interfacial energy is too low, the active compound is bonded firmly by the polymer matrix; release of effective amounts at the surface does not take place. If the physico-chemical compatibility of the active compound and matrix is good, a high diffusion coefficient of the active compound in the polymer is achieved. The level of the release rate of the antimicrobially active substance in this case can be regulated by varying the amount of active compound incorporated, since the amount of active compound released is then proportional to the concentration in the matrix.

Combinations of matrix and active compound which have an interfacial energy of 0.5 to 30 mN/m, particularly preferably 5 to 15 mN/m, are preferably chosen for preparation of the copolyesters according to the invention comprising active compounds.

The copolyesters according to the invention comprising active compounds are distinguished in that they have a molecularly disperse distribution of the pharmacologically active substance in the polymeric matrix. It has been possible to demonstrate the high morphological homogeneity of the extruded plastics containing active compounds with the aid of light and scanning electron microscope photographs. It has furthermore been possible to demonstrate with the aid of scanning electron microscope photographs that the polymer has a smooth surface before and after release of the active compound incorporated, i.e. the biocompatibility of the polymer surface is impaired neither by the addition nor by the release of the active compound.

The mechanical properties of the polymer also are not impaired by the addition of the pharmacologically active substances in amounts of 0.1 to 5 wt. %. For certain material/active compound combinations an improvement in the mechanical properties is even observed.

Comparable samples comprising active compounds which were produced by means of the cast film method (solvent casting), on the other hand, are significantly more inhomogeneous. Scanning electron microscope studies demonstrate that the active compounds incorporated are partly present in the polymer matrix and on the surface in the form of crystal associations. The crystal associations have the effect of impairing the mechanical properties of the polymer. The crystal associations dissolved out moreover leave behind a rough surface, which leads to a reduced biocompatibility.

The shaped articles according to the invention can be produced by extruding a melt comprising the polymer and active compound. The melt can comprise 0.01 to 10 wt. %, preferably 0.1 to 5 wt. % of active compound. The components can be mixed by known techniques in any manner. For example, the active compound can be incorporated directly in solid form into the polymer melt. A masterbatch comprising the active compound can also be melted directly with the polymer or mixed with the already existing polymer melt. The active compound can also be applied to the polymer by means of known techniques (by tumbling, spraying etc.) before melting of the polymer.

The mixing/homogenizing of the components moreover can be carried out by known techniques via kneaders or screw machines, preferably in single- or twin-screw extruders in a temperature range of between 150 and 200° C.

By mixing the components during the extrusion process a homogeneous, molecularly disperse distribution of the active compound in the polymer matrix is achieved without additional working steps having been necessary.

Shaping is carried out by the known techniques of thermoplastic processing (injection moulding, tube take-off etc.). The shaped articles are free from specks, flexible and non-tacky and can be sterilized without problems by the usual processes.

EXAMPLES

Example 1 (comparison)

Commercially available copolyester: Hytrel® (DuPont, Wilmington, Del. 19880-0709)

Example 2

10 g active compound were applied to 990 g Hytrel® containing no active compound in an intensive mixer. The cylindrical granules comprising the active compound were extruded on a ZSK1 twin-shaft extruder. A homogeneous melt free from specks was obtained and, after cooling in a water/air bath and granulation of the strand, gave uniform cylindrical granules.

For microbiological in vitro studies and for determination of the release profile of the active compound incorporated, the granules were in each case injection-moulded to test specimens (sheets).

| Example | Active compound incorporated |
|---------|------------------------------|
| 2a | kanamycin disulfate |
| 2b | gentamicin sulfate |
| 2c | ciprofloxacin-betaine |
| 2d | doxycycline HCl |
| 2e | clindamycin HCl |
| 2f | lincomycin HCl |
| 2g | fusidic acid |
| 2h | bacitracin |

Example 3

50 g kanamycin disulfate were applied to 950 g Hytrel® containing no active compound in an intensive mixer. The cylindrical granules comprising the active compound were extruded on a ZSK1 twin-shaft extruder. A homogeneous melt free from specks was obtained and, after cooling in a water/air bath and granulation of the strand, gave uniform cylindrical granules.

Example 4

To prepare a masterbatch comprising the active compound, 380 g of cylindrical granules of the copolyester Hytrel®containing no active compound were dissolved in chloroform, and 20 g kanamnycin disulfate were added. The mixture was heated (approx. 70° C.) until a colourless, homogeneous solution was obtained. After removal of the solvent at 65° C./15 mbar, colourless, slightly opaque polymer sheets were obtained and were comminuted with the aid of a chopping machine.

400 g of the 5 wt. % masterbatch were mixed with 1,600 g of cylindrical granules containing no active compound and the mixture was extruded on a ZSK1 twin-shaft extruder. A homogeneous melt free from specks was obtained and, after cooling in a water/air bath and granulation of the strand, gave uniform cylindrical granules.

Example 5

To prepare a masterbatch comprising the active compound, 380 g of cylindrical granules of the copolyester Hytrel®containing no active compound were dissolved in chloroform, and 20 g gentamycin sulfate were added. The mixture was heated (approx. 70° C.) until a colourless, homogeneous solution was obtained. After removal of the solvent at 65° C./1 5 mbar, colourless, slightly opaque polymer sheets were obtained and were comminuted with the aid of a chopping machine.

400 g of the 5 wt. % masterbatch were mixed with 1,600 g of cylindrical granules containing no active compound and the mixture was extruded on a ZSK1 twin-shaft extruder. A homogeneous melt free from specks was obtained and, after cooling in a water/air bath and granulation of the strand, gave uniform cylindrical granules.

Example 6

To prepare a masterbatch comprising the active compound, 380 g of cylindrical granules of the copolyester Hytrel® containing no active compound were dissolved in chloroform, and 20 g bacitracin were added. The mixture was heated (approx. 70° C.) until a colourless, homogeneous solution was obtained. After removal of the solvent at 65° C./15 mbar, colourless, slightly opaque polymer sheets were obtained and were comminuted with the aid of a chopping machine.

400 g of the 5 wt. % masterbatch were mixed with 1,600 g of cylindrical granules containing no active compound and the mixture was extruded on a ZSK1 twin-shaft extruder. A homogeneous melt free from specks was obtained and, after cooling in a water/air bath and granulation of the strand, gave uniform cylindrical granules.

Example 7

S2 tensile bars were stamped out of the test specimen sheets of the materials prepared in examples 1, 2a and 2b and the characteristic strength values were determined in accordance with DIN 53 455. The tension sets of the test specimens were determined in accordance with DIN 53 518. The moduli of elasticity were determined in accordance with DIN 53 457.

The results of the studies are summarized in the table. They document that the level of the thermo-mechanical properties of Hytrel® without a filler content is not substantially changed by addition of antimicrobially active substances.

TABLE 1

Level of thermo-mechanical properties of Hytrel without a filler content and of Hytrel samples containing active compound.

| Measurement values | Example 1 Hytrel ® | Example 2a Hytrel ® + 1 wt. % kanamycin | Example 2b Hytrel ® + 1 wt. % gentamicin |
|---|---|---|---|
| Tensile strength [MPa] | 13.9 | 11.5 | 12.6 |
| Elongation at break [%] | 934 | 681 | 755 |
| Residual elongation at 200% elongation | 62 | 59 | 62 |
| E'(10° C.) [MPa] | 68 | 61 | 61 |
| E'(36° C.) [MPa] | 61 | 54 | 54 |

Example 8

The release profiles of polymer samples comprising active compounds were determined by elution in Millipore water (0.1% NaN$_3$). For this, in a typical experiment 20 ml Millipore water were added at 37° C. to 5 g of polymer platelets of Hytrel® (area: 1 cm$^2$) comprising active compound and the mixture was stirred at a constant speed. The eluting agent was removed at regular intervals of time of 24 h for quantitative determination of the active compound content and replaced by fresh Millipore water. The active compound released was quantified in the corresponding solutions via HPLC analysis. All the series of experiments were carried out 2-fold and the quantitative determination of the active compound content was in each case carried out as a duplicate determination.

The results of the studies are summarized in table 1. They document that the polymers comprising active compounds release the corresponding antimicrobially active substance at the surface continuously over a relatively long period of time (2 weeks). It was furthermore possible to show that the diffuision of the active compound out of the polymer can be utilized as an adjustable release mechanism: The higher the amount of active compound incorporated, the greater the concentration of active compound released from the polymer matrix in the elution medium.

Table 2:

Release profiles of polymer samples comprising active compounds. In each case the concentration [mg/l] of the active compound released from the polymer sample is stated.

Example 1: Control sample of Hytrel® containing no active compound, Example 2c: 1.0 wt. % ciprofloxacin-betaine in Hytrel®, Example 2d: 1.0 wt. % doxycycline HCl in Hytrel®, Example 2e: 1.0 wt. % clindamycin HCl in Hytrel®, Example 2f: 1.0 wt. % lincomycin HCl in Hytrel®, Example 2g: 1.0 wt. % fusidic acid in Hytrel®.

| Time [h] | 0 | 24 | 48 | 72 | 96 | 168 | 192 | 216 | 240 | 264 |
|---|---|---|---|---|---|---|---|---|---|---|
| Example 1 | 0 | 0 | 0 | 0 | 0 | 0 | 0 | 0 | 0 | 0 |
| Example 2c | 0 | 190 | 261 | 316 | 357 | 420 | 446 | 465 | 484 | 501 |
| Example 2d | 0 | 387 | 557 | 672 | 771 | 884 | 930 | 961 | 986 | 1003 |
| Example 2e | 0 | 1532 | 1899 | 2220 | 2455 | 2795 | 2897 | 2978 | 3052 | 3113 |
| Example 2f | 0 | 487 | 630 | 754 | 849 | 1051 | 1105 | 1154 | 1205 | 1247 |
| Example 2g | 0 | 4.3 | 6.1 | 8.3 | 10.7 | 13.4 | 16.7 | 20.0 | 23.5 | 27.5 |

Example 9

The antimicrobial activity of the modified polymers was tested on the bacteria strains *S. epidermidis* 0–47- and *S. epidermidis* 0–47+(bioMeriuex D-72622 Nuirtingen) and the test strains *S. aureus* ATCC 25923, *S. epidermidis* ATCC 14990 and *S. saproph.* ATCC 43867.

The bacteria strains were in each case cultured in an overnight culture on standard 11 nutrient agar (Merck KGaA, D-64293 Darmstadt) and suspended in NaCl solution (0.85%). The resulting bacteria suspension with a density of 0.5 MacFarland was diluted 1:100 in NaCl solution (0.85%) and applied to agar plates (Mueller-Hinton agar, Merck KGaA, D-64293 Darmstadt). The polymer samples 1 cm$^2$ in size were sterilized, laid on the agar plates under a slight pressure and incubated at 37° C. for 20 hours. After the incubation the agar plates were checked for inhibitory areolas and the inhibitory areolas were measured.

21 test series (3 different polymer samples against 7 test strains) were carried out. The results of the agar diffusion test are summarized in table 2. They show that, in contrast to the sample containing no active compound, an inhibitory zone in which no bacterial growth takes place was formed around the polymer samples comprising active compounds, i.e. the polymer samples comprising active compounds have a substantial antimicrobial action against the test strains used.

TABLE 3

Testing of the antimicrobial activity of polymer samples containing no active compound and comprising active compounds against various test strains in the agar diffusion test. The antimicrobial action is indicated by the formation of an inhibitory areola. The inhibitory areola diameters are stated in mm.

|  | S. epid. 0–47-* | S. epid. 0–47+* | S. aureus 851 | S. aureus ATCC 25923 | S. epid. ATCC 14990 | S. saproph. ATCC 43867 |
|---|---|---|---|---|---|---|
| Example 1 Hytrel ® (control) | 0 | 0 | 0 | 0 | 0 | 0 |
| Example 2a Hytrel ® + 1.0 wt. % kanamycin | >19 | >19 | 0 | >19 | >19 | >19 |
| Example 2b Hytrel ® + 1.0 wt. % gentamicin | >19 | >19 | >19 | >19 | >19 | >19 |

*) Source: bioMeriuex, D-72622 Nürtingen

What is claimed is:

1. A composition comprising:
    (a) an aromatic copolyester that includes,
        (i) 15–65 wt % of the copolyester of an ester unit of the formula (I)

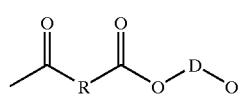

(I)

wherein
        R represents a divalent radical of a dicarboxylic acid which has a molecular weight of less than about 350,
        D represents a divalent radical of an organic diol which has a molecular weight of less than about 250, and
        (ii) 35–85 wt % of the copolyester of an ester unit of the formula (II)

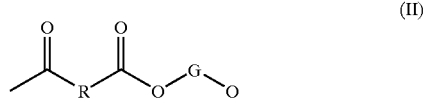

wherein
        R represents a divalent radical of a dicarboxylic acid which has a molecular weight of less than about 350,
        G represents a divalent radical of a long-chain glycol which has an average molecular weight of about 350 to 6,000;
    and
    (b) at least one homogeneously distributed antimicrobially active substance selected from the group consisting of quinolones, aminoglycosides, macrolides, polypeptides lincomycins antimycobacterial agents, fusidic acid, nalidixic acid, pipemidic acid, cinoxacin, ciprofloxacin, norfloxacin, ofloxacin, pefloxacin, enoxacin, gentamycin, kanamycinm amikacin, sisomycin, tobramycin, netilmicin, erythromycin, clarithromycin, azithromycin, bacitracin, mupirocin, thrythricin, lincomycin, clindamycin and rifampicin.

2. A process for the preparation of the composition of claim 1 comprising, mixing homogeneously said antimicrobially active substance (b), and said aromatic copolyester (a).

3. A shaped article comprising:
    (a) an aromatic copolyester that includes
        (i) 15–65 wt % of the copolyester of an ester unit of the formula (I)

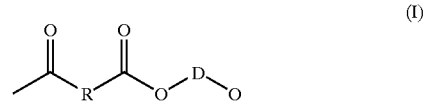

wherein
        R represents a divalent radical of a dicarboxylic acid which has a molecular weight of less than about 350,
        D represents a divalent radical of an organic diol which has a molecular weight of less than about 250, and
        (ii) 35–85 wt % of the copolyester of an ester unit of the formula (II)

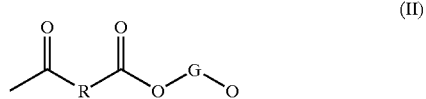

wherein
        R represents a divalent radical of a dicarboxylic acid which has a molecular weight of less than about 350,
        G represents a divalent radical of a long-chain glycol which has an average molecular weight of about 350 to 6,000;
    and
    (b) at least one homogeneously distributed antimicrobially active substance.

4. A thermoplastic molding composition comprising:
(a) an aromatic copolyester that includes,
  (i) 15–65 wt % of the copolyester of an ester unit of the formula (I)

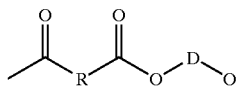
(I)

wherein
  R represents a divalent radical of a dicarboxylic acid which has a molecular weight of less than about 350,
  D represents a divalent radical of an organic diol which has a molecular weight of less than about 250, and
  (ii) 35–85 wt % of the copolyester of an ester unit of the formula (II)

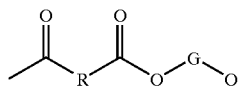
(II)

wherein
  R represents a divalent radical of a dicarboxylic acid which has a molecular weight of less than about 350,
  G represents a divalent radical of a long-chain glycol which has an average molecular weight of about 350 to 6,000;
and
(b) at least one homogeneously distributed antimicrobially active substance.

5. A molded article comprising the thermoplastic molding composition of claims 4.

6. A method of making a medical article comprising, molding the composition of claim 1 into the medical article.

7. The aromatic copolyester of the composition of claim 1, wherein the dicarboxylic acid comprises 8 to 16 carbon atoms.

8. The composition of claim 1, wherein the dicarboxic acid of said aromatic copolyester is selected from the group consisting of phthalic acid, terephthalic acid and isophthalic acid.

9. The composition of claim 1, wherein the organic diol of said aromatic copolyester comprises 2 to 15 carbon atoms.

10. The composition of claim 1, wherein the organic diol of said aromatic copolyester is selected from the group consisting of ethylene, propylene, tetramethylene, isobutylene, pentamethylene, 2,2-dimethyltnmethylene, hexamethylene and decamethylene glycols, dihydroxycyclohexane, cyclohexanedimethanol, resorcinol and hydroquinone.

11. The composition of claim 1, wherein the long chain glycol of said aromatic copolyester comprises 2 to 9 carbon atoms.

12. The composition of claim 1, wherein the long chain glycol of said aromatic copolyester is selected from the group consisting of glycol esters of poly-(alkylene oxide)-dicarboxylic acids or polyester glycols, polyformals, polythloether glycols, polybutadiene glycols and polyisoprene glycols.

* * * * *